United States Patent [19]

Lojek

[11] Patent Number: 5,573,997
[45] Date of Patent: Nov. 12, 1996

[54] HERBICIDAL COMPOSITION CONSISTING ESSENTIALLY OF ACETIC ACID AND CITRIC ACID

[75] Inventor: John S. Lojek, Elmira, Canada

[73] Assignee: Ecoval Inc., Montreal, Canada

[21] Appl. No.: 190,201

[22] PCT Filed: Aug. 6, 1992

[86] PCT No.: PCT/CA92/00342

§ 371 Date: Jul. 18, 1994

§ 102(e) Date: Jul. 18, 1994

[87] PCT Pub. No.: WO93/02555

PCT Pub. Date: Feb. 18, 1993

[30] Foreign Application Priority Data

Aug. 8, 1991 [GB] United Kingdom ............... 9117114

[51] Int. Cl.$^6$ .............. A01N 37/02; A01N 37/04
[52] U.S. Cl. ............................................ 504/142
[58] Field of Search ................... 504/320, 142

[56] References Cited

U.S. PATENT DOCUMENTS 3,869,277  3/1975  Berger et al. ............... 71/113
4,529,797  7/1985  Peik et al. ................. 536/123

FOREIGN PATENT DOCUMENTS 4030687  5/1991  Germany.

OTHER PUBLICATIONS

Abstract of JP 62–176922. 1987.

*Primary Examiner*—S. Mark Clardy
*Attorney, Agent, or Firm*—Sim & McBurney

[57] ABSTRACT

An aqueous herbicidal composition consisting essentially of about 1–5 wt. % acetic acid and 0.25 to 2.5 wt. % citric acid in a ratio of acetic:citric of about 4:1 to about 2:1.

13 Claims, No Drawings

HERBICIDAL COMPOSITION CONSISTING ESSENTIALLY OF ACETIC ACID AND CITRIC ACID

This application has been filed under 35 USC 371 from PCT/CA92/00342 filed Aug. 6, 1992.

FIELD OF INVENTION

The present invention relates to herbicidal compositions.

BACKGROUND TO THE INVENTION

Many herbicidal compositions exist which are effective to kill all vegetation or selective vegetation. Many are based on sophisticated chemicals, some of which are toxic to other life forms.

SUMMARY OF INVENTION

In accordance with the present invention, there is provided a novel herbicidal composition which is composed of edible material and hence can be safely applied to vegetation without risk of harm to animals, including humans.

GENERAL DESCRIPTION OF INVENTION

The composition of the invention can be formulated to effectively kill all vegetative growth, including normally hard-to-kill weeds as well as grasses, in a rapid period of time. Alternatively, the composition may be formulated as a selective herbicide, for example, to kill common lawn weeds, while leaving the grass unaffected. The composition of the invention also is useful as a defoliant.

The composition of the invention comprises a synergistic combination of acetic acid and another organic acid, preferably citric acid. The acetic acid component conveniently is provided by domestic white vinegar while the citric acid is conveniently provided by lemon juice or the juice of another citrus fruit. Industrial sources of these components also may be used.

The composition of the invention may be formulated as a concentrate comprising glacial acetic acid and citric acid or other organic acid, such as ascorbic acid, dissolved in water, which then may be diluted for use.

Although acetic acid alone exhibits some effect as a herbicide, the presence of small quantities of citric acid considerably enhances the effect. Citric acid at high concentrations exhibits some effect as a herbicide.

The weight ratio of acetic acid to citric acid in the composition may vary from about 10:1 to about 1:1, preferably about 4:1 to about 2:1. In general, with the presence of an increasing quantity of citric acid for the same quantity of acetic acid, there is an increasing activity to a maximum, at which addition of further quantities of citric acid produces no further effect. The composition in use may contain up to about 10 wt % of acetic acid, preferably about 1 to about 5 wt. %. The composition in use may contain about 0.25 to about 2.5 wt % citric acid.

The activity of the combination of acetic acid and citric acid may be enhanced further by the presence of small quantities of wetting agents, which preferably are edible emulsifiers.

A particularly-useful composition according to the invention comprises about 2 parts vinegar and about 1 part of lemon juice or other citrus fruit juice. This composition is diluted with water to provide the composition ready for use.

The degree of dilution of the composition determines whether the herbicidal composition will kill all vegetation and whether it is selective.

One composition which has been found useful as a total vegetation kill composition comprises:

500 mls of vinegar 250 mls of lemon juice 750 to 1250 mls of water

If the dilution is increased to about 2300 mls of water, the composition becomes a selective herbicide. Too much dilution results in no herbicidal properties. For example, dilution by 5000 mls of water produces no herbicidal response.

Another useful composition comprises:

10 wt. % glacial acetic acid 5 wt. % citric acid 85 wt. % water

One useful formulation of concentrate comprises:

160 g acetic acid 40 g citric acid 800 ml water

This concentrate then is diluted for use to the desired strength.

By experimentation, it is possible to determine the degree of dilution required for specific properties of the composition for varying proportions of acetic acid and citric acid.

The composition of the invention is composed of natural and edible components, namely acetic acid and citric acid or other organic acid, and hence, not only is efficacious as a herbicide, either for total or selective kill of vegetation, but is safe to use. In contrast, most herbicides require chemical synthesis and exhibit toxic side effects on animals.

SUMMARY OF DISCLOSURE

In summary of this disclosure, the present invention relates to a novel herbicidal composition comprising synergistic combinations of acetic acid and citric acid, most conveniently provided by vinegar and lemon juice, which are diluted with water to provide the desired herbicidal properties. Modifications are possible within the scope of this invention.

What we claim is:

1. An aqueous herbicidal composition for application to vegetative growth to achieve a selective or complete kill of the vegetative growth, consisting essentially of, in use, from about 1 to about 5 wt. % of acetic acid and from about 0.25 to about 2.5 wt. % of citric acid and wherein the weight ratio of said acetic acid to said citric acid is about 4:1 to about 2:1.

2. The composition of claim 1 formulated as a concentrate for dilution for use.

3. The composition of claim 1 or 2 wherein a wetting agent additionally is present in the composition.

4. The composition of claim 1 suitable for a complete kill of vegetative growth consisting essentially of:

500 mls of vinegar 250 mls of lemon juice 750 mls to 1250 mls of water.

5. The composition of claim 1 suitable for a selective kill of vegetative growth consisting essentially of:

500 mls of vinegar 250 mls of lemon juice 3300 mls to 1250 mls of water.

6. The composition of claim 1 consisting essentially of:

10 wt. % glacial acetic acid 5 wt. % citric acid 85 wt. % water.

7. The composition of claim 1 formulated as a concentrate for dilution for use consisting essentially of:

160 g acetic acid 40 g citric acid 800 mls water.

8. A method of controlling post-emergent vegetative growth, which comprises applying to said vegetative growth an aqueous herbicidal composition consisting essentially of acetic acid and citric acid, said citric acid being present in said composition in a herbicidal activity enhancing amount and said acetic acid and citric acid being present in said composition in proportions sufficient to achieve a desired degree of kill to said vegetative growth.

9. The method of claim 8 wherein said herbicidal composition contains a weight ratio of acetic acid to citric acid of about 10:1 to about 1:1.

10. The method of claim 9 wherein said weight ratio is about 4:1 to about 2:1.

11. The method of claim 8 wherein said aqueous herbicidal composition contains up to about 10 wt. % acetic acid.

12. The method of claim 11 wherein said citric acid is present in an amount of from about 1 to about 5 wt. %.

13. The method of claim 12 wherein said citric acid is present in an amount of about 0.25 to about 2.5 wt. %.

* * * * *